United States Patent [19]

Greuter et al.

[11] 4,061,644
[45] Dec. 6, 1977

[54] PROCESS FOR THE PRODUCTION OF 2-AMINO-3-HYDROXYPYRIDINES

[75] Inventors: Hans Greuter, Eiken; Daniel Bellus, Riehen, both of Switzerland

[73] Assignee: Ciba-Geigy Corporation, Ardsley, N.Y.

[21] Appl. No.: 697,603

[22] Filed: June 18, 1976

[30] Foreign Application Priority Data

June 27, 1975 Switzerland .................. 8379/75

[51] Int. Cl.$^2$ .................................. C07D 213/74
[52] U.S. Cl. ...................................... 260/296 R
[58] Field of Search ...................... 260/296 R, 297 R

[56] References Cited

U.S. PATENT DOCUMENTS 3,579,528  5/1971  Haszeldine et al. ............. 260/296 R

OTHER PUBLICATIONS

Klingsberg, Pyridine and Its Derivatives, Part Three, frontispage, pp. 563 to 564, 566 and 726–727, Interscience Publishers (1962).
Dunlop et al., The Furans, frontispage, pp. 527, 528, 533, 671–673, Reinhold Publishing Corp. NY, (1953).
Aso, Chemical Abstracts, vol. 34, col. 6940 (1940), (abst. of J. Agr. Chem. Soc. Japan 16, pp. 253–264 (1940).
Petersen et al., Chemical Abstracts, vol. 69, abst. No. 59063 a, pp. 5518 to 5519, (1968).

Primary Examiner—Alan L. Rotman
Attorney, Agent, or Firm—Harry Falber

[57] ABSTRACT

Process for the production of 2-amino-3-hydroxypyridines of the formula

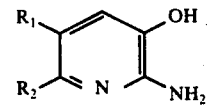

wherein $R_1$ and $R_2$ independently of one another represent hydrogen or an alkyl group having 1 to 4 carbon atoms, wherein a furan-2-carboxylic acid of formula

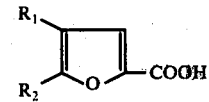

wherein $R_1$ and $R_2$ have the meaning given above, or a derivative thereof, for example a quaternary ammonium salt, an ester, an amide, a halogenide, an amidine salt, an iminoether salt or the nitrile, is reacted at a temperature of between 100° and 300° C in a solvent containing amide groups, in the presence of an acid catalyst, with ammonia.

6 Claims, No Drawings

PROCESS FOR THE PRODUCTION OF 2-AMINO-3-HYDROXYPYRIDINES

The present invention relates to a novel process for the production of 2-amino-3-hydroxypyridines, and to the 2-amino-3-hydroxypyridines obtained by this process.

Various processes for producing 2-amino-3-hydroxypyridines starting with other pyridine derivatives are known from the literature. 2-Amino-3hydroxypyridines optionally substituted in the 5- or 6-position by a methyl group can be produced, for example, by nitration of the corresponding 3-hydroxypyridines with fuming nitric acid in the presence of concentrated sulphuric acid, and reduction of the resulting nitropyridines in the presence of palladiumcharcoal catalysts or in the presence of hydrazine hydrate and Raney nickel [see J.Chem.Soc., 1957, 4625–27; Swiss Pat. Spec. No. 452,529 and German 'Offenlegungsschrift'No. 2,330,109]. According to the German 'Offenlegunsschrift' No. 2,245,363, 2-amino-3-hydroxypyridines which are substituted in the 5- and/or 6-position by alkyl groups having 1 to 4 carbon atoms can be obtained also by reaction of the corresponding 3-hydroxypyridines with sodium amide at elevated temperature. 2-Amino-3-hydroxypyridine can be produced, in a multi-stage process, also by reaction of furfural with chlorine or with an agent releasing chlorine, reaction of the resulting reaction product with sulphamic acid to give 3-hydroxy-2-imino-1-(2H)-pyridine-sulphonic acid-monohydrate, and hydrolysis of this compound [see Swiss Pat. Spec. No. 466,279].

These known processes are disadvantageous insofar as relatively expensive starting products (pyridines) and/or several process stages are required to perform them. Furthermore, the yields obtained with these known processes are in some cases unsatisfactory, or considerable amounts of undesirable by-products, such as inorganic salts, occur.

It has now been found that 2-amino-3-hydroxypyridines of formula I

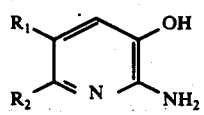

(I)

wherein
$R_1$ and $R_2$ independently of one another represent hydrogen or an alkyl group having 1 to 4 carbon atoms can be produced in an appreciably simpler and more economic manner and in good yields by a process in which a furan derivative of formula II

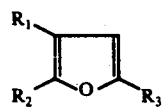

(II)

wherein
$R_1$ and $R_2$ have the meaning given under formula I, and
$R_3$ represents a group $-COO^-M^+$, $-COO-X$,

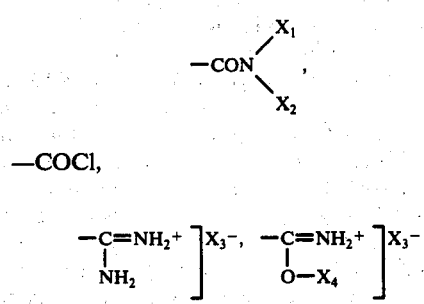

or $-CN$, whereby
$M^+$ denotes

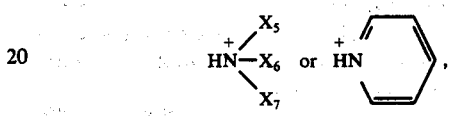

X, $X_1$ and $X_2$ independently of each other represent hydrogen, an unsubstituted or substituted alkyl group, an alkenyl, cycloalkyl, phenyl, benzyl or phenylethyl group, or a $-CH_2$-cycloalkyl group or $-CH_2$-oxacycloalkyl group, $X_3^-$ represents $-Cl^-$, $Br^-$ or $F^-$, $X_4$ represents an unsubstituted alkyl group, an allyl, cycloalkyl, benzyl or phenylethyl group, and $X_5$, $X_6$ and $X_7$ independently of one another represent hydrogen or an alkyl group having 1 to 4 carbon atoms, is reacted at a temperature of between 150° and 300° C in a solvent containing amide groups, in the presence of an acid catalyst, with ammonia.

Alkyl radicals denoted by the symbols $R_1$, $R_2$, X, $X_1$, $X_2$ and $X_4$ to $X_7$ can be straight-chain or branched-chain.

Alkyl groups X, $X_1$, $X_2$ and $X_4$ preferably contain 1–8, especially 1–4, carbon atoms.

If alkyl groups X, $X_1$ and $X_2$ are substituted, the substituents concerned are, in particular, halogen atoms such as chlorine, bromine or fluorine, nitro groups, amino groups, alkoxy groups, N-alkylamino groups or N,N-dialkylamino groups, the alkoxy group and each alkyl group having 1–4 carbon atoms, especially 1 or 2 carbon atoms, in the alkoxy or alkyl moieties.

Alkenyl groups X, $X_1$ and $X_2$ preferably contain 3 or 4 carbon atoms.

If X, $X_1$, $X_2$ or $X_4$ denote cycloalkyl groups, or if substituents X, $X_1$ and $X_2$ contain cycloalkyl moieties, the groups in question are, in particular, those having 3–8 carbon atoms.

Preferably, $R_1$ represents hydrogen and $R_2$ represents methyl, especially however hydrogen. $R_3$ represents in particular a group $-COO-X$;

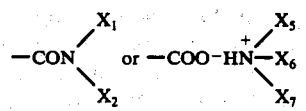

wherein X hydrogen or an unsubstituted alkyl group having 1–4, especially 1 or 2, carbon atoms, and $X_1$, $X_2$, $X_5$, $X_6$ and $X_7$ independently of one another represent hydrogen, methyl or ethyl.

The furan derivatives of formula II are known, or can be produced by methods known per se.

Suitable solvents containing amide groups are, for example, unsubstituted acyclic or cyclic amides, or acyclic or cyclic amides mono- or disubstituted on the nitrogen atom by alkyl groups having 1-4 carbon atoms, especially 1 or 2 carbon atoms, or by phenyl groups, or unsubstituted amidines, particularly:

- unsubstituted amides, or amides substituted as defined, of saturated aliphatic, optionally substituted monocarboxylic acids, especially those having 1-8 carbon atoms in the acid moiety, such as formamide, acetamide, propionic acid amide, butyric acid amide, valeramide, capronic acid amide, caprylic acid amide, N,N-dimethyl- and N,N-diethylformamide, N,N-dimethyl- and N,N-diethylacetamide, N,N-dimethyl-methoxyacetamide and N-methyl-N-phenylacetamide;
- amidines of saturated aliphatic monocarboxylic acids having 1-3 carbon atoms in the acid moiety, such as formamidine and acetamidine;
- unsubstituted amides, or amides substituted as defined, of saturated or insaturated aliphatic, optionally substituted, dicarboxylic acids, especially those having 2-10 carbon atoms in the acid moiety, such as oxamide, succinic acid diamide, malonic acid diamide, methoxy-malonic acid diamide and tetramethyldiamide of fumaric acid;
- unsubstituted amides of cycloaliphatic monocarboxylic acids, such as cyclohexanecarboxylic acid amide;
- unsubstituted amides of aromatic mono- or dicarboxylic acids optionally ring-substituted by alkyl or alkoxy groups having 1 or 2 carbon atoms, or by nitro groups, such as benzamide, 4-nitrobenzamide, 3-methoxybenzamide and phthalimide;
- unsubstituted amides, or amides substituted as defined, of carbonic acid or of derivatives thereof, such as urethane, ethylurethane, urea, tetramethylurea and dimorpholinocarbonyl;
- unsubstituted amides, or amides substituted as defined, of phosphorous acid, of phosphoric acid, of phenylphosphonic acid or of aliphatic phosphonic acid having 1-3 carbon atoms in the acid moiety, such as phosphoric acid triamide, phosphoric acid-tris-(dimethylamide) (hexametapol), phosphoric acid trimorpholide, phosphoric acid-tripyrrolidide, phosphoric acid-bis-(dimethylamide)-morpholide, phosphoric acid-dimethylamide-diethylamide-morpholide, phosphoric acid-bis-(diethylamide)-morpholide, phosphoric acid-tris-(dimethylamide), tetramethyldiamide of methanephosphonic acid and hexamethyltriamide of phosphoneacetic acid;
- unsubstituted amides, or amides substituted as defined, of sulphuric acid, or of aliphatic or aromatic sulphonic acids such as tetramethylsulphamide, dimethylamide of methanesulphonic acid or p-toluenesulphonic acid amide;
- cyclic amides such as N-methyl-2-pyrrolidone, N-acetyl-2-pyrrolidone or M-methyl-ε-caprolactam.

Preferred solvents containing amide groups are formamide, acetamide, N,N-dimethylformamide, N,N-dimethylacetamide, N-methyl-2-pyrrolidone and phosphoric acid-tripyrrolinide, more especially however phosphoric acid-tris-(dimethylamide).

According to one procedure of the process of the invention, the solvents containing amide groups can also be formed in situ in the presence of excess ammonia, i.e. from other solvents which under the reaction conditions convert to solvents containing amide groups, particularly esters and nitriles of the aforementioned aliphatic, cycloaliphatic and aromatic carboxylic acids, esters of carbonic acid, phosphoric acid, phosphorous acid, esters of aromatic or aliphatic phosphonic acids, sulphuric acid esters, esters of aliphatic or aromatic sulphonic acids. Suitable esters are, in particular, alkyl esters having 2-5 carbon atoms, or phenyl and benzyl ester.

The following examples may be mentioned: formic acid methyl ester, acetic acid methyl ester and butyric acid methyl ester, formic acid ethyl ester, acetic acid ethyl ester and butyric acid ethyl ester, and formic acid benzyl ester, acetic acid benzyl ester and butyric acid benzyl ester; benzoic acid ethyl ester, benzoic acid isobutyl ester, acetonitrile, propionitrile, methoxypropionitrile, adipic acid dinitrile, sebacic acid dinitrile, cyclohexanecarboxylic acid nitrile, benzonitrile; carbonic acid dimethyl ester, carbonic acid diethyl ester and carbonic acid diphenyl ester, triethyl phosphate, triethyl phosphite, dibutyl phosphite, ethanephosphonic acid diethyl ester, diethyl sulphate and p-toluenesulphonic acid ethyl ester.

Nitriles of saturated aliphatic monocarboxylic acids having 1-3 carbon atoms in the acid moiety are preferred for the production in situ of solvents containing amide groups, in the presence of excess ammonia. Particularly preferred is acetonitrile.

The above-mentioned solvents containing amide groups can be diluted with other solvents. Solvents that can be used for this purpose are, for example: water; monohydric or dihydric aliphatic alcohols having up to 6 carbon atoms, such as methanol, ethanol, n-butanol or ethylene glycol; aliphatic and aromatic hydrocarbons, such as n-pentane, n-hexane, benzene, xylenes or nitrobenzene; aliphatic and cycloaliphatic ketones, such as acetone, methyl ethyl ketone, cyclopentanone and cyclohexanone; aliphatic and cyclic ethers, such as diethyl ether, ethylene glycol monomethyl ether, ethylene glycol dimethyl ether, ethylene glycol diethyl ether, tetrahydrofuran, tetrahydropyrane and dioxane; tetrahydrothiophene dioxide (sulpholane); and dialkyl sulphoxides, such as dimethyl sulphoxide and diethyl sulphoxide.

Acid catalysts advantageously used in the process of the invention are protonic acids, salts of a protonic acid with ammonia or with an organic base containing nitrogen, or Lewis acids.

Examples of suitable protonic acids are: optionally halogenated, saturated or unsaturated, aliphatic monocarboxylic acids preferably having 1-8 carbon atoms, such as formic acid, acetic acid, propionic acid, butyric acid, adipic acid, acrylic acid, methacrylic acid, chloroacetic acid, dichloroacetic acid, trichloroacetic acid and trifluoroacetic acid; alkylsulphuric acids, such as methylsulphuric acid; optionally substituted aliphatic or aromatic sulphonic acids, such as methanesulphonic acid, benzenesulphonic acid, p-toluenesulphonic acid, naphthalenesulphonic acid or naphthalene-1,5-disulphonic acid; aliphatic or aromatic phosphonic or phosphonic acids, such as methyl-, benzyl- or phenylphosphonic acid or dimethyl- or diethylphosphonic acid, diethylphosphinic acid and benzenephosphinic acid; inorganic acids, such as hydrohalic acids, e.g. hydrochloric acid, hydrobromic acid and hydrofluoric acid; nitric acid, phosphoric acid and sulphuric acid.

Suitable salts of such protonic acids with an organic base containing nitrogen are, in particular, salts with amines of the formula

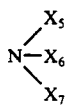

and pyridinium salts, whereby $X_5$, $X_6$ and $X_7$ have the meanings given under formula II.

Preferred salts are the ammonium salts of hydrohalic acids, especially ammonium chloride.

Depending on the nature of the starting materials used, the stated salts can also be formed in situ from these starting materials.

The reaction of furan derivatives of formula II with ammonia can also be performed in the presence of Lewis acids, i.e. acids which can receive an electron pair. Suitable Lewis acids are, e.g., aluminum chloride and aluminium bromide, calcium chloride, tin tetrachloride, titanium tetrachloride, iron(III) chloride, zinc chloride, boron trifluoride, phosphorus trichloride and antimony pentafluoride or antimony pentachloride.

The acid catalyst is generally used in an amount of about 5-20 percent by weight, relative to the furan derivative of formula II.

The reaction of the furan derivatives of formula II with ammonia is in general performed in a closed system, and preferably at a temperature of between 150° and 300° C, especially between about 200° and 260° C.

In carrying out the process of the invention, there is used at least the stoichiometric amount of ammonia, i.e. 2 moles of ammonia per mole of the furan derivative of formula II. The process of the invention is however advantageously performed in the presence of excess ammonia. An excess of 3 of 30 moles of ammonia has in practice proved satisfactory.

In the case where the solvent containing amide groups is produced in situ, the minimum amount of ammonia increases by the amount which is consumed, in the formation of the solvent containing amide groups, from the respective solvent used.

After the reaction, the compounds of formula I are isolated in a manner known per se and optionally purified, e.g. by sublimation, chromatography or crystallisation.

The compounds of formula I are known. They constitute valuable starting products for the production of azo dyestuffs [see U.S. Pat. No. 3,419,570 and German 'Offenlegungsschrift' No. 2,236,269]; or for the production of pharmaceutical preparations; or for the production of insecticidal active substances. [see U.S. Pat. No. 3,808,218].

It is possible by the process of the invention to produce the compounds of formula I in good yields, in one stage and with the use of readily available cheap starting products. The process is advantageous also from an ecological point of view in that undesirable inorganic salts are not formed or are formed only in small amounts.

EXAMPLE 1

42.0 g (0.3 mole) of furan-2-carboxylic acid ethyl ester, 3.0 g of ammonium chloride, 60 ml of phosphoric acid-tris(dimethylamide) (hexametapol) and 51 g (3.0 moles) of ammonia are heated in a 300 ml autoclave for 10 hours at 230° C. After cooling to about 20°-25° C, the reaction mixture is rinsed from the autoclave with water and acetone. An aliquot of the reaction solution is taken in order to determine the crude yield of 2-amino-3-hydroxypyridine. By means of a thin-layer-chromatographical comparison with calibration solution, the crude yield is shown to be 50±5%. The bulk of the solvent is removed in a rotary evaporator, and the residue is chromatographed on 150 g of silica gel with methylene chloride containing 5 percent by volume of methanol. The fractions finally eluted yield, after concentration by evaporation, 17.2 g (52% of theory) of pure 2-amino-3-hydroxypyridine; m.p. 171°-173° C.

EXAMPLE 2

37.8 g (0.3 mole) of furan-2-carboxylic acid methyl ester, 3.0 g of ammonium bromide, 60 ml of hexametapol and 51 g (3.0 moles) of ammonia are heated in a 300 ml autoclave for 9 hours at 230° C. The crude yield of 2-amino-3-hydroxypyridine, after cooling to about 20-25° C, is 50±5%. The reaction mixture is adjusted to pH 1-2 by the addition of 3N sulphuric acid, and is then repeatedly washed with methylene chloride. The reaction mixture is subsequently brought to pH 7 with 10% sodium hydroxide solution, and then continously extracted with diethyl ether. After concentration of the extracts by evaporation, the residue is sublimated to yield 15.8 g (48% of theory) of pure 2-amino-3-hydroxypyridine, m.p. 170°-173° C.

EXAMPLE 3

33.3 g (0.3 mole) of furan-2-carboxylic acid amide, 51 g (3.0 moles) of ammonia, 3.0 g of ammonium chloride and 60 ml of hexametapol are heated, in the manner described in the preceding Examples, for 4.5 hours at 230° C. Crude yield determined by thin layer chromatography: 60±5%; yield of pure 2-amino-3-hydroxypyridine after processing as described in Example 1: 19.7 g (60% of theory); m.p. 170°-173° C.

EXAMPLES 4-19

In a 300 ml autoclave, there is reacted in each case 0.05 mole of each of the furan-2-carboxylic acid derivatives given in the following Table, in 10 ml, or 10 g of solvent, with 20 g (1.18 moles) of ammonia under the reaction conditions shown in the Table. The crude yields obtained after the reaction are determined by thin-layer chromotography.

Table

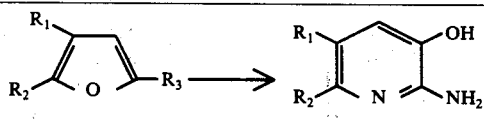

| Example No. | $R_1$ | $R_2$ | $R_3$ | Solvent | Catalyst (g) | Temperature °C | Reaction time (hrs) | Crude yield % of theory |
|---|---|---|---|---|---|---|---|---|
| 4 | H | H | —COOCH$_2$CH$_3$ | hexametapol | NH$_4$Cl (0,5) | 240 | 8 | 50 |
| 5 | H | H | —COOH | hexametapol | NH$_4$Cl (0,5) | 240 | 11 | 45 |

Table-continued

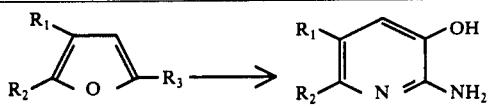

| Example No. | R₁ | R₂ | R₃ | Solvent | Catalyst (g) | Temperature °C | Reaction time (hrs) | Crude yield % of theory |
|---|---|---|---|---|---|---|---|---|
| 6 | H | H | —COOCH₂CH₃ | acetonitrile | NH₄Cl (0,5) | 240 | 10 | 45 |
| 7 | H | H | —CONH₂ | hexametapol | NH₄Cl (0,5) | 240 | 5 | 55 |
| 8 | H | H | —CN | hexametapol | NH₄Cl (0,5) | 220 | 5 | 35 |
| 9 | H | H | —COOCH₂CH₃ | hexametapol | NH₃Br (0,5) | 230 | 9 | 45 |
| 10 | H | H | —COOCH₂CH₃ | dimorpholino-carbonyl | NH₄Cl (0,5) | 240 | 10 | 45 |
| 11 | H | H | 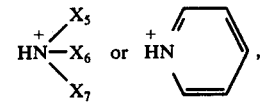 | hexametapol | NH₄Cl*)(2,67) | 200 | 5 | 35 |
| 12 | H | H | —COOCH₂CH₃ | hexametapol | ZnCl₂ (0,7) | 230 | 6 | 40 |
| 13 | H | H | —COOCH₂CH₃ | phosphoric acid-tris-morpholide | NH₄Cl (0,5) | 240 | 11 | 45 |
| 14 | H | H | —COOCH₂CH₃ | urea | NH₄Cl (0,5) | 220 | 7 | 35 |
| 15 | H | H | —COOCH₃ | hexametapol | NH₄Cl (0,5) | 240 | 8 | 50 |
| 16 | H | CH₃ | —COOCH₃ | hexametapol | NH₄Cl (0,5) | 240 | 10 | 30 |
| 17 | H | CH₃ | —CN | hexametapol | NH₄Cl (0,5) | 240 | 8 | 30 |
| 18 | H | CH₃ | —CN | hexametapol | NH₄Br (1,0) | 230 | 10 | 30 |
| 19 | H | H | —COOCH₃ | hexametapol | NH₄Cl (0,5) | 250 | 3 | 45 |

*formed in situ from reactants

We claim:
1. Process for the production of 2-amino-3-hydroxy-pyridines of formula I

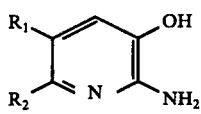

wherein R₁ and R₂ independently of one another represent hydrogen or an alkyl group having 1 to 4 carbon atoms,
in which process a furan derivative of formula II

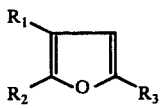

wherein
R₁ and R₂ have the meaning given under formula I, and R₃ represents a group COO⁻M⁺, —COO—X,

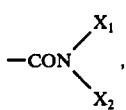

—MCOCL,

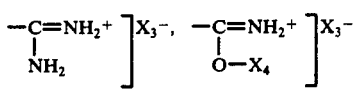

or —CN,
whereby
M+ denotes $$\underset{X_7}{\overset{X_5}{\underset{|}{HN{-}X_6}}}\quad \text{or} \quad \overset{+}{HN}\diagup\hspace{-0.5em}\diagdown ,$$

X, X₁ and X₂ independently of each other represent hydrogen, an unsubstituted or substituted alkyl group, an alkenyl, cycloalkyl, phenyl, benzyl, or phenylethyl group, or a —CH₂-cycloalkyl group or —CH₂-oxacycloalkyl group, X₃⁻ represents —Cl⁻ or Br⁻ or F⁻, X₄ represents an unsubstituted alkyl group, an allyl, cycloalkyl, benzyl or phenylethyl group, and X₅, and X₆ and X₇ independently of one another represent hydrogen or an alkyl group having 1 to 4 carbon atoms, is reacted with ammonia in a closed reaction system at a temperature of between 100° and 300° C in a solvent containing amide groups selected from the group consisting of formamide, acetamide, N,N-dimethylformamide, N,N-dimethylacetamide, N-methyl-2-pyrrolidone, phosphoric acid tripyrrolidide and phosphoric acid-tris-(dimethylamide), in the presence of an acid catalyst selected from the group consisting of aliphatic C₁-C₈ mono-carboxylic acids, halogenated aliphatic C₁-C₈ mono-carboxylic acids, alkylsulfuric acids, aliphatic sulfonic acids, aromatic sulfonic acids, aliphatic phosphonic acids, aliphatic phosphinic acids, aromatic phosphonic acids, aromatic phosphinic acids, hydrohalic acids, nitric acid, phosphoric acid, sulfuric acid and ammonium salts of hydrohalic acids, and Lewis acids selected from the group consisting of aluminum chloride, aluminum bromide, calcium chloride, tin tetrachloride, titanium tetrachloride, iron (III) chloride, zinc chloride, boron trifluoride, phosphorus trichloride, antimony pentafluoride and antimony pentachloride.

2. Process according to claim 1, wherein the employed solvent is produced under the reaction conditions in the presence of excess ammonia, from acetonitrile.

3. Process according to claim 1, wherein the reaction is performed in the presence of ammonium chloride.

4. Process according to claim 1, wherein the reaction is performed at temperatures of between 200° and 260° C.

5. Process according to claim 1, wherein there is used a furan derivative of formula II in which $R_1$ represents hydrogen, and $R_2$ represents methyl or especially hydrogen.

6. Process according to claim 1, wherein there is used a furan derivative of formula II in which $R_1$ and $R_2$ each represent hydrogen, and $R_3$ represents a group —COO—X,

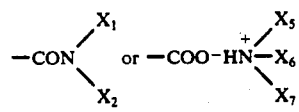

and X represents hydrogen or an unsubstituted alkyl group having 1 to 4 carbon atoms, and $X_1$, $X_2$, $X_5$, $X_6$ and $X_7$ independently of one another represent hydrogen, methyl or ethyl.

* * * * *